United States Patent [19]
Clarke et al.

[11] Patent Number: 4,862,886
[45] Date of Patent: Sep. 5, 1989

[54] LASER ANGIOPLASTY
[75] Inventors: Richard H. Clarke, Scituate; Jeffrey M. Isner, Weston; David F. Muller, Boston, all of Mass.
[73] Assignee: Summit Technology Inc., Watertown, Mass.
[21] Appl. No.: 731,961
[22] Filed: May 8, 1985
[51] Int. Cl.$^4$ ............................................. A61B 17/36
[52] U.S. Cl. ............................... 128/303.1; 128/398; 350/96.2; 372/53; 372/57; 372/70; 372/108
[58] Field of Search ..................... 128/303.1, 395–398; 372/53, 57, 70, 71, 108, 109; 350/96.2

[56] References Cited

U.S. PATENT DOCUMENTS

| | | | |
|---|---|---|---|
| 4,207,874 | 6/1980 | Choy . | |
| 4,233,493 | 11/1980 | Nath | 128/398 X |
| 4,432,600 | 2/1984 | Falco | 320/96.2 X |
| 4,448,188 | 5/1984 | Loeb . | |
| 4,532,400 | 7/1985 | Toida et al. | 128/303.1 |
| 4,576,177 | 3/1986 | Webster | 128/660 |
| 4,580,557 | 4/1986 | Hertzmann | 128/395 |
| 4,641,650 | 2/1987 | Mok | 128/303.1 |
| 4,641,912 | 2/1987 | Goldenberg | 350/96.10 |
| 4,669,465 | 6/1987 | Moore et al. | 128/303.1 |
| 4,669,467 | 6/1987 | Willett et al. | 128/303.1 |
| 4,686,979 | 8/1987 | Gruen et al. | 128/303.1 |
| 4,784,132 | 11/1988 | Fox et al. | 128/303.1 |
| 4,800,876 | 1/1989 | Fox et al. | 128/303.1 |

FOREIGN PATENT DOCUMENTS

| | | | |
|---|---|---|---|
| 144764 | 6/1985 | European Pat. Off. . | |
| 2548354 | 5/1977 | Fed. Rep. of Germany | 128/303.1 |
| 8603598 | 6/1986 | PCT Int'l Appl. . | |
| 2076993 | 12/1981 | United Kingdom | 128/303.1 |
| 8301893 | 6/1983 | World Int. Prop. O. | 128/303.1 |

OTHER PUBLICATIONS

Linsker et al., "Far-UV Laser Ablation . . . ", Lasers in Surgery and Medicine 4:201-206, 1984, *Lamba-Physik*, EMG 150 E/EJ, 5/1983.
Uchino et al., "Efficient Dye Lasers . . . ", Appl. Phys. 19, No. 1, 35-37, May 1979.
Burlamacchi et al., "A Simple Reliable Waveguide Dye Laser", Review of Sc. Inst., vol. 46, No. 3, p. 281-283, Mar. 1975.
Marcruz et al., "Possibilidades Terapeuticas do Raio Laser em Ateromas", vol. 34, Aro Bras Cardiol, pp. 9-12, (1980).
Lee et al., "Laser Dissolution of Coronary Atherosclerosis Obstruction", vol. 102, Amer. Heart J., pp. 1074-1075, (1980).
Abela et al., "Effects of Carbon Dioxide, Nd:Yag, and Argon Laser Radiation on Coronary Atherosclerosis Plaques," vol. 5, Amer J. Cardiol, pp. 1199-1205 (1982).
Choy et al., "Transluminal Laser Catheter Angioplasty" vol. 50, Amer. J. Cardiol, pp. 1206-1208, (Dec. 1982).
Choy et al., Laser Coronary Angioplasty "Experience with 9 Cadaver Hearts", Amer. J. Cardiol, vol. 50, pp. 1209-1211, (1982).
Ginsberg et al., "Salvage of an Ischemic Limb by Laser Angioplasty, Description of a New Technique", vol. 7, Clin. Cardiol, pp. 54-58 (1984).
Isner & Clark, "The Current Status of Lasers in the Treatment of Cardiovascular Disease", vol. QE-20, No. 12, IEEE J. Quantum Electronics, pp. 1406-1414 (1984).
Abela et al., "Laser Recanalization of Occuluded Atherosclerotic Arteries in Vivo and In Vitro", vol. 71, Circulation, pp. 403-422 (1985).

*Primary Examiner*—Lee S. Cohen
*Attorney, Agent, or Firm*—Thomas J. Engellenner

[57] ABSTRACT

A laser therapy system having improved effectiveness in surgical use, particularly in laser angioplasty, can be formed by employing a pulsed source of radiation. The pulsed energy source is preferably an excimer laser having a coherent beam of ultraviolet radiation and preferably is employed in conjunction with a dye laser to produce an output beam which is tunable over a wide portion of the ultraviolet and visible spectrum. The output beam is coupled via a novel coupling device to an optical fiber disposed within a surgical instrument, for example, a percutaneous catheter. The operative components are sealed in a gas-tight, liquid-tight housing. An electronic controller monitors and adjusts the output energy density, duration, and pulse repetition rate. In operation, a pulsed, high energy beam of extremely short duration is available to remove atherosclerotic plague with less damage to the underlying tissue and less chance of perforating the blood vessel wall.

20 Claims, 3 Drawing Sheets

LASER ANGIOPLASTY

BACKGROUND OF THE INVENTION

This invention concerns surgical instruments and procedures and, in particular, systems, devices and methods for performing laser surgery (e.g., angioplasty) to treat atherosclerosis and the like.

Atherosclerosis is a disease which causes the thickening and hardening of the arteries, particularly the larger artery walls. It is characterized by lesions of raised fibrous plaque which form within the arterial lumen. The plaques are most prevalent in abdominal aorta, coronary arteries and carotid arteries and increase progressively with age. They commonly present dome-shaped, opaque, glistening surfaces which bulge into the lumen. A lesion typically will consist of a central core of lipid and necrotic cell debris, capped by a collagen fibromuscular layer. Complicated lesions will also include calcific deposits and various degrees of necrosis, thrombosis and ulceration.

The deformities of the arterial lumen presented by the plaque and associated deposits result in occluded blood flow, higher blood pressure and ultimately ischemic heart disease, if untreated. In 1984, coronary atherosclerosis was still the leading cause of death in the United States, claiming the lives of over a half million Americans annually, roughly twice as many as are killed by cancer.

The treatment of coronary atherosclerosis presently consists of drug therapy, thoracic surgery and percutaneous angioplasty. Drug therapy is primarily directed to the control of hypertension with diuretics, antiadrenergic agents, vasodilators and angiotension blockers. The goal of the drug therapy is to return the arterial pressure to normal levels and thereby reduce the stress on the patient's heart, kidneys and other organs. Unfortunately, drug therapy is not without side effects and cannot be relied upon to control progressive or acute atherosclerosis.

In the more serious instances of coronary atherosclerosis, thoracotomies are typically performed and so called "bypass" operations are conducted. In the bypass procedure, a vein (usually from the patient's leg) is utilized to construct a detour around the occluded coronary artery. One end of the vein is attached to the aorta, and the other end is attached to occluded vessel just beyond the obstruction. Although bypass surgery has become an accepted surgical procedure, it presents substantial morbidity risks, involves costs ranging from $25,000 to $40,000 in 1984 dollars, and generally requires extended hospitalization. Moreover, the procedure is often limited to arteries proximal to the heart and the long-term prognosis is less than satisfactory. Roughly 5 percent of the bypass grafts can be expected to occlude with each year following the operation; during this time it is not uncommon for the native artery to also become completed occluded as well, necessitating repeated procedures.

Recently, small balloon-tipped catheters have been developed which can be passed percutaneously into various arteries and inflated to dilate areas of partial obstruction. While this procedure has gained a measure of acceptance as a less invasive alternative to bypass surgery, balloon angioplasty simply redistributes the atherosclerosis stenoses; the frequency of reoccurence may be as high as 30 percent and such reoccurences further increase both as a function of the number of lesions treated and the time post-angioplasty.

Laser therapy has been suggested as another approach to angioplasty. For example, in a proposed procedure a catheter carrying a fiber optic waveguide is passed into an occluded blood vessel, positioned proximal to an atherosclerstic lesion and activated to decompose the plaque. Devices along these lines have been disclosed, for example, in U.S. Pat. No. 4,207,874 issued to Choy on June 17, 1980; and U.S. Pat. No. 4,448,188 issued to Loeb on May 15, 1984. See also generally, Marcruz et al., "Possibilidades Terapeuticas do Raio Laser em Ateromas," Vol 34, No. 9, Arq Bras Cardiol, (1980); Lee et al., "Laser Dissolution of Coronary Atherosclerosis Obstruction, Vol. 102, Amer Heart J, pp. 1074–1075 (1980); Abela et al., "Effects of Carbon Dioxide, Nd:YAG, and Argon Laser Radiation on Coronary Atherosclerosis Plaques,", Vol. 5, Amer J Cardiol, pp. 1199–1205 (1982); Choy et al., "Transluminal Laser Catheter Angioplasty" Vol. 50, Amer J Cardiol, pp. 1206–1208 (December 1982); Choy et al "Laser Coronary Angioplasty: Experience with 9 cadaver hearts," Amer J Cardiol, Vol. 50, pp. 1209–1211, (1982); Ginsberg et al., "Salvage of An Ischemic Limb by Laser Angioplasty, Description of a New Technique," Vol. 7, Clin Cardiol, pp. 54–58 (1984); Isner and Clark, "The Current Status of Lasers in the Treatment of Cardiovascular Disease", Vol. QE-20, No. 12, IEEE J Quantum Electronics, pp. 1406–1414 (1984); and Abela et al., "Laser Recanalization of Occluded Atherosclerotic Arteries In Vivo and In Vitro," Vol. 71, Circulation pp. 403–422 (1985), the teachings of which are incorporated herein by reference.

At present the use of laser angioplasty almost entirely has been restricted to animal studies and in vitro experiments on vessels obtained from human donors post mortem. The few reports of human therapy appear to confirm the feasibility of the procedure but the patency of arteries recannalized using present laser therapy techniques remains to be proven. A number of difficulties and adverse side effects also have emerged from the studies to date. Many of the attempts on excised blood vessels have resulted in charred tissue, coagulation necrosis and/or polymorphous lacunae. These pathological injuries suggest that blood vessels treated by laser angioplasty will require significant healing time periods and may be left with scarred, thrombogenic surfaces. Moreover, two other serious problems with present techniques are thermal and mechanical perforation. These perforations occur most commonly in connection with calcific deposits, branch points and torturous coronary arterial segments. Branch points and torturous coronary segments lead to mechanical and thermal perforations when they cause the optical fiber not to be coaxial with the artery.

Several histopathologic features of atherosclerotic arterial segments contribute directly to the problem of mechanical-thermal perforations. First, collagen is a principal component of atherosclerotic plaque. Because collagen typically imparts a white hue to the intimal surface of the plaque, the output of at least one commercially available laser system, the argon laser with its 454-514 nm blue-green light, is not preferentially absorbed. Second, calcification of the plaque further diminishes absorbance. Consequently, when the optical fiber initiates vaporization of plaque, the fiber will often "track" away from the calcified, severely fibrotic portions of the plaque toward the "softer" portions of the plaque, such as foci of yellow pultaceous debris or well developed (red) vascularity. These sites constitute a potential path of least resistance, which not infrequently promotes eccentric fiber-penetration of plaque into the highly absorbant (red) media and then, the outer adventitia. The result is perforation. Third, because the principal component of the media, smooth muscle, is characteristically depleted or attentuated in segments of atherosclerotic coronary arteries, a limited margin for error exists between the target of vaporization (i.e., plaque) and the underlying arterial wall.

There exists a need for better methods and devises for performing angioplasty. A system which could selectively remove complicated plaque lesions and associated materials from the arterial lumen with minimal injury to the underlying tissue and less risk of thermal or mechanical perforation would represent a substantial improvement. A system suitable for use in a surgical environment, with its components sealed to patient exposure and set to operate within a predefined range of optimal conditions, would satisfy a significant need in the art.

SUMMARY OF THE INVENTION

It has been discovered that a laser therapy system having improved effectiveness in surgical use, particularly in laser angioplasty, can be formed by employing a pulsed source of radiation. The pulsed energy source is preferably an excimer laser having a coherent beam of ultraviolet radiation and preferably is employed in conjunction with a dye laser to produce an output beam which is tunable over a wide portion of the ultraviolet and visible spectrum The output beam is coupled via an optical fiber to the surgical instrument, for example, a percutaneous catheter In operation, a pulsed, high energy beam of extremely short duration is available to remove atherosclerotic plague with less damage to the underlying tissue and less chance of perforating the blood vessel wall.

In one aspect of the invention, the unique properties of excimer energy sources are exploited. "Excimer" is a coined word, used to describe the physical operation of certain gas lasers which typically contain noble gas-halide combinations as the active medium. In operation, an electrical discharge or ionizing field is applied to the medium and energy is absorbed by the individual atoms, thereby raising them to a higher energy state. The electrical excitation of one of the atoms (i.e. the halogen) initiates bonding with the other atomic species (i.e. xenon or krypton) resulting in the formation of an electronically "excited dimer" or "excimer". As the molecule returns to its ground state, short wavelength (and correspondingly high energy) ultraviolet radiation is emitted. In one preferred embodiment, a Xenon-Hydrogen Chloride-Neon excimer medium is employed with suitable buffer gases in a mode-locked or Q-switched configuration. Another useful medium is Xenon-Fluoride-Neon. Various other combinations can also be employed and may be preferred for particular applications. The precise wavelength emitted by the excimer energy source can be varied by choice of the gas mixture.

In particular applications it may also be preferred to employ pulsed energy sources other than excimer lasers. The pulsed laser medium can be gaseous, liquid or solid state. Rare earth-doped solid state lasers, ruby lasers, alexandrite lasers, carbon dioxide lasers, Nd: YAG lasers and Ho:YLF lasers are all examples of lasers that can be operated in a pulsed mode and used in the present invention.

The term "pulsed" is used herein to describe lasers which generate peak powers on the order of 100 kilowatts per square centimeter or greater (with peak power being defined in terms of pulse energy over pulse length) Preferably the peak power of the pulsed radiation source is at least 500 kilowatts per square centimeter. Also preferably, the pulse length of the output pulse is about 1 microsecond or less. Typically, the laser medium is excited by a capacitive discharging flash lamp or similar fast excitation source.

The operation of the pulsed laser provides a substantial improvement to laser angioplasty. Until now researchers have been applying continuous wave ("CW") radiation to atherosclerotic plague with limited success. Thermal injury of the laser irradiated surfaces has been a consistent consequence of CW laser irradiation. Grossly thermal injury is manifested by charring that is easily recognized by non-magnified visual inspection. Under the microscope, the effects of CW irradiation are characteristically evidenced by coagulation necrosis and polymorphous lacunae. In contrast, similar experiments on excised blood vessels with pulsed radiation reveals no gross or microscopic evidence of thermal injury. The high peak energy density and extremely short duration of excimer radiation appears to greatly reduce the thermal effects outside of the path of the laser beam. Thus, the invention can be employed in angioplasty to avoid necrosis and lacunae, facilitate a more benign healing process and less thrombogenic surfaces, and in general better preserve structure and tissue integrity. Moreover, by accomplishing lesion vaporization without non-target heating, the invention also can be expected to reduce the principal complication of laser angioplasty, blood vessel wall perforation.

In another aspect of the invention, a tunable dye laser is pumped by the pulsed laser to produce an output beam which can be tuned, for example, from about 300 nanometers to about 1000 nanometers in wavelength. In a preferred embodiment, an eximer laser and dye laser combination are designed to operate at about 307 nanometers or greater to avoid the potential mutagenic or tumorigenic risks that have been suggested may result from exposure to shorter wavelength UV radiation. A dye laser of open cavity design is preferable (i.e., no intra cavity tuning elements) to promote high conversion efficiency. The dye laser can consist of a rectangular flowing dye cell within a kinematic mount to facilitate easy changes of the dye, making both tuning and degraded dye replacement rapid and safe.

Suitable dyes for use in the dye laser components of the invention include, for example, P-terphenyl (peak wavelength 339); BiBuQ (peak wavelength: 385); DPS (peak wavelength: 405); and Coumanin 2 (peak wavelength: 448). In addition, the excimer-dye laser system is preferably designed to allow the user to bypass the dye cell and extract the excimer pump beam directly for particular applications. Thus, for example, a Xenon-Hydrogen Chloride-Neon excimer laser can be applied without the dye laser to provide a high energy radiation source at about 307-308 nanometers.

In a further aspect of the invention, the operative components of the invention are sealed in a gas tight, liquid tight housing to insure against patient or user exposure in the surgical setting. Nonetheless, the system is designed for ready manipulation by practitioners and technicians during use. In a preferred embodiment, an electronic controller monitors and adjusts the output energy density, duration, and pulse repetition rate. Similarly, the controller can monitor the state of the excimer gas and the laser dye to indicate when replacement is necessary. The controller can also be connected to manual or foot controls, adjustment knobs, visual displays and paper printouts. Preferably, the housing also includes a filter to trap waste gases and fittings to receive sealed canisters or cartridges for dye replacements.

The output beam from the system preferably has a peak energy density ranging from about 0.2 to about 20 Joules per square centimeter, preferably from about 0.5 to about 10 Joules per square centimeter. The pulse duration preferably ranges from about 5 nanoseconds to about 100 nanosecond and the period between pulses can vary from about 1 millisecond to about 1 second.

The output beam is coupled to a catheter to deliver laser therapy through a receptacle, hermetically sealed to the housing of the laser system, having an opening adapted to receive a optical waveguide (i.e., a light-transmitting fiber) which passes into the catheter. The coupling device also includes a fastening means for releasably fastening the waveguide in a precise position in the receptacle during use and for releasing the waveguide once the laser therapy is completed. Moreover, the coupling device can include a focusing means formed within the receptacle for receiving the beam of radiation from the laser system and focusing the radiation into the waveguide fiber. The receptacle preferably is designed such that the circumferential periphery of the waveguide fiber is protected from the incident laser radiation by a mask or the like in order to avoid chipping or otherwise damaging the fiber when high energy, radiation pulses are focussed into the waveguide fiber.

Catheters, useful in practicing laser angioplasty with the laser system of the present invention, can take various forms. For example, one embodiment can consist of a catheter having an outer diameter of 3.5 millimeters or less, preferably 2.5 millimeters or less. Disposed within the catheter is the optical fiber for delivery of the laser therapy which can be a 100-200 micron diameter silica (fused quartz) fiber such as the model SG 800 fiber manufactured by Spectran, Inc. of Sturbridge, Masss. The catheter is preferably multi-lumen to provide flushing and suction ports. In one embodiment the catheter tip can be constructed of radio-opaque and heat resistant material, incorporating a transducer for either an ultrasound or microwave source of imaging. The radio-opaque tip can be used to locate the catheter under fluoroscopy. The catheter can also include an inflatable balloon, such as that described in U.S. Pat. No. 4,448,188 issued to Loeb on May 15, 1984 or in International patent application No PCT/US82/01669 by G. Lee filed on Nov. 30, 1982, or in an article by Gruntzig et al., "Nonoperative Dilation of Coronary Artery Stenoses: Percutaneous Transluminal Angioplasty", Vol. 301, *New England Journal of Medicine*, pp. 66–68 (1979), each of which is incorporated herein by reference. In use the balloon can be inflated periodically to stop blood flow for viewing and/or laser therapy, to allow saline flushing or to remove debris by suction. Additionally, the catheter can include a steering means such as that disclosed in U.S. Pat. No. 3,470,876 issued to Barchilon on Oct. 7, 1969, also incorporated herein by reference. The catheter should be readily sterilizable and preferably is disposable.

The invention will next be described in connection with certain illustrated embodiments. However, it should be clear that various changes and modifications can be made by those skilled in the art without departing from the spirit or scope of the invention. For example, various other pulsed lasers can be substituted for the excimer source. Various gas mixtures can be employed in the excimer laser. For examples of particular excimer laser media and configurations, see U.S. Pat. Nos. 34,426,706 issued to Liu et al.; 4,393,505 issued to Fahlen; 4,348,647 issued to Nigham et al.; and 4,340,968 issued to Willis et al., herein incorporated by reference. Similarly, various dye materials can be used in the dye laser. Configurations other than a free-flowing dye , such as dye-impregnated plastic films or curvette-encased dyes, can be substituted in the dye laser. The dye laser can also store a plurality of different dyes and substitute one for another automatically in response to user-initiated control signals or conditions encountered during angioplasty (e.g. when switching from a blood-filled field to a saline field or in response to calcific deposits).

The invention can be used with various catheter devices, including devices which operate under fluoroscopic guidance as well as devices which incorporate imaging systems, such as echographic or photoacoustic imaging systems or optical viewing systems. For one example of a photoacoustic imaging system which can be specifically adapted for the catheter environment, see U.S. Pat. No. 4,504,727 incorporated herein by reference. When an optical viewing system is employed, the laser system can also generate a beam of visible light for illumination purposes and the catheter can also be designed to provide a focusing spot so that a user viewing the field can precisely determine the focal point of the therapeutic UV radiation beam. It may also be preferred to employ various fluorogenic agents within the blood vessel for imaging purposes including fluorogenic agents that are selectively absorbed by the plaque deposits. Additionally, it may be preferred to practice the invention in conjunction with the administration of hematorporphyrins or other agents that are selectively taken up by plaque materials and aid in lyzing the lesion when activated by the laser radiation.

Although the principal use described herein is laser angioplasty, it should also be clear that the laser therapy system of the present invention can also be coupled to other surgical instruments besides catheters designed for percutaneous passage into an arterial lumen. The invention can also be employed in conjunction with a laser scalpel for general operative procedures or in conjunction with an endoscope for tracheal or gastric operation. Moreover, the laser therapy system can be used with intra-operative cardiac catheters to perform procedures such as myotomies or myectomies within the heart or to debride calcific deposits on the aortic valves.

DETAILED DESCRIPTION

Figure 1:
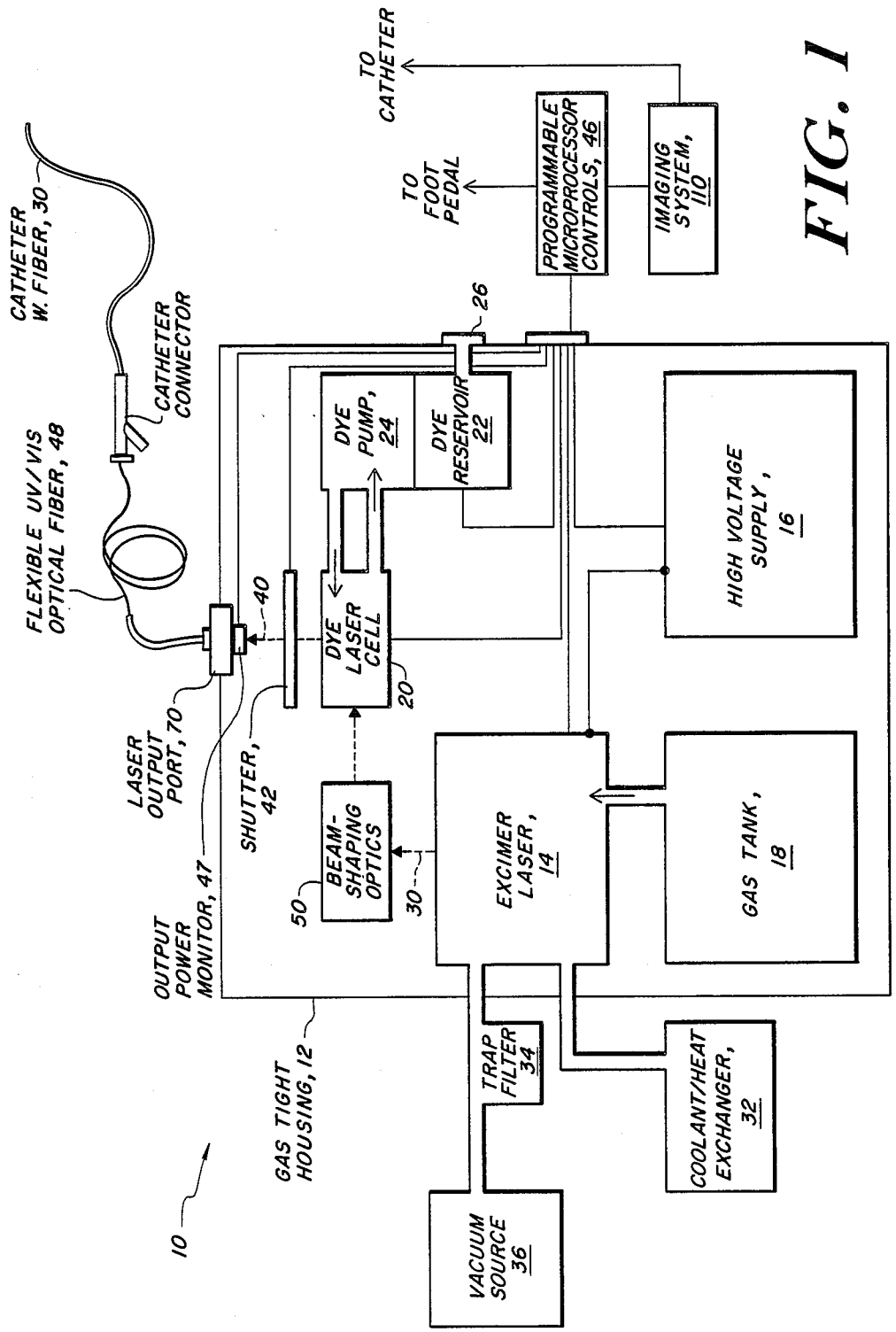
FIG. 1 is a schematic block diagram of a laser therapy system according to the invention.

FIG. 1 shows an overall block diagram of the laser therapy system 10 of the present invention consisting of a housing 12 which encases a pulsed laser (i.e., an excimer laser) 14 together with its high voltage power supply 16 and the excimer gas storage tank 18. Also disposed within the housing 12 is a dye laser cell 20 which is pumped by the output beam 30 of the excimer laser 14. In addition to the dye laser cell 20 (discussed in more detail below) the housing 12 also encloses a dye reservoir 22 and a dye pump 24. The housing is designed to provide a sealed, gas-tight, liquid-tight enclosure to ensure against patient or user exposure in the surgical setting. The illustrated excimer laser is cooled by a heat exchanger 32 external to the housing 12 via a circulating coolant. An external vacuum source 36 is also provided to maintain the excimer medium under the proper conditions for lasing. A trap filter 34 can be incorporated into the vacuum line in order to remove any gas contaminants and/or aid in gas replacement. The housing 12 is also fitted with a dye substitution port 26 to allow rapid and safe dye replacement or substitution.

In operation, the high voltage supply 16 under microprocessing control 46 excites the gas in the excimer laser 14 to yield an output beam 30. This excimer output beam 30 is shaped by a lens system 50 and directed into the dye laser cell 20 wherein it reacts with the flowing dye to yield a dye laser output 40 which is focused on laser output port 70 for focusing into the optical fiber 48 disposed within catheter 80. A foot pedal or manual control (not shown) is connected to microprocessor 46. Shutter 42 is also connected to microprocessor 46 and, when open, allows the output beam 40 to pass into the output port 70. The microprocessor 46 is also connected to an output power monitor 47. Both the excimer laser 14 and the dye laser 20 as well as the dye pump 24 and the high voltage supply 16 are also continuously monitored by the microprocessor 46 which can be programmed to yield an output beam of a particular power, pulse duration, wavelength and exposure time. Microprocessor 46 can also be connected to an imaging system 110, such as an optical, echographic or photoacoustic imaging system, and can automatically shut down the output beam 40 in response to detected changes in the image signal, e.g., changes that would indicate a danger of arterial wall perforation.

Figure 2:
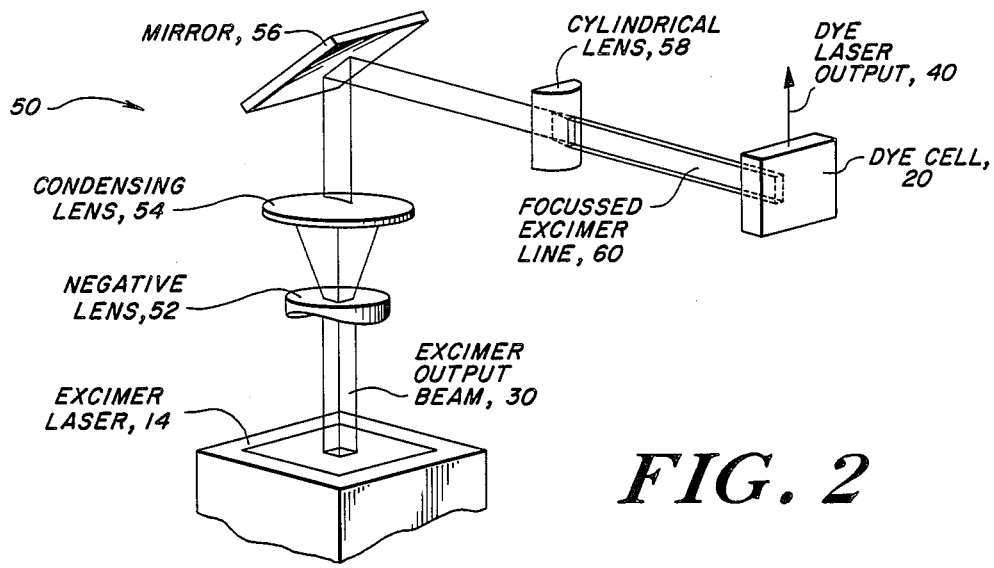
FIG. 2 is a detailed schematic diagram of the excimer laser beam shaping optics of the system shown in FIG. 1.

In FIG. 2, a more detailed schematic diagram of the excimer laser beam shaping optics 50 is shown, consisting of a first negative lens 52 and a subsequent condensing lens 54 which together form a Gallilean telescope. In one preferred embodiment, the power of the telescope is 4 to 6 times magnification. The effect of the two telescopic lenses 52, 54 is to take a nominally square beam of about 1 cm $\times$ 1 cm dimension and spread the beam out to a width of 4 to 6 cm. In the illustrated embodiment, this magnified beam is then reflected off of mirror 56 and passed through a cylindrical lens 58 having a 6 to 10 cm focal length. The effect of the cylindrical lens 58 is to focus the magnified beam to a line focus of about 4–6 centimeters long and 0.5–1.0 mm high. This focussed line 60 acts as the dye laser pump to produce dye laser output beams 40.

Figure 3:
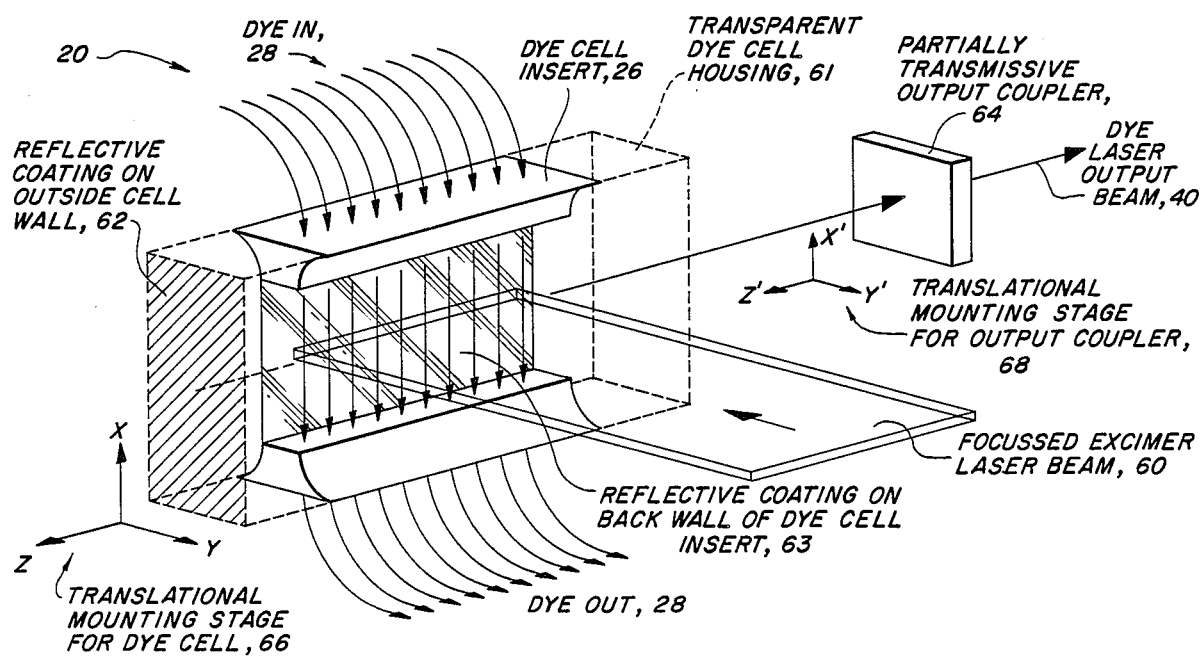
FIG. 3 is a detailed schematic diagram of the dye cell of the system shown in FIG. 1.

In FIG. 3, the details of one dye cell configuration are illustrated. Although the illustration shows a vertically free-flowing dye 28 and a horizontal output beam 40, it should be appreciated that other configurations are equally feasible and that in particular applications it may be preferable to pass the dye horizontally through the cell 20 and produce a vertical output beam. In FIG. 3, a dye cell 20 is shown, consisting of a hollow cell housing 61 and a cell insert 26. The cell insert is designed with funnel-shaped or beveled inlets and outlets to permit the flowing dye 28 to pass through the cell. The insert 26 also includes general reflective coating 63 on its back wall, (i.e. an aluminized coating), to reflect the focused excimer laser beam 60 back into the dye for additional pumping. The housing 61 is designed to be transmissive to excimer radiation in the ultraviolet region of the spectrum (i.e. a quartz cell housing). As shown in FIG. 3, the effect of the pump beam 60 is to induce lasing in the dye 28 within cell 20. A reflective coating on 62 on the outside wall of housing 61 forms one reflective surface of a resonant cavity and a partially transmissive output coupler 64 forms the other wall. The resonant cavity defined by these two reflectors yields a dye laser beam aligned along the Z axis. It is also preferred to mount one end of the dye cell 20 on a translational stage 66 such that motion in the X or Y direction of the stage will permit slight tilting of the dye cell (i.e. in the XZ or YZ directions for precise alignment). Similarly, the output coupler 64 is also mounted on a translational stage 68 for alignment purposes. In one preferred embodiment, the output coupler can include a spatial filter and thereby, improve the spatial quality of the beam.

Figure 4:
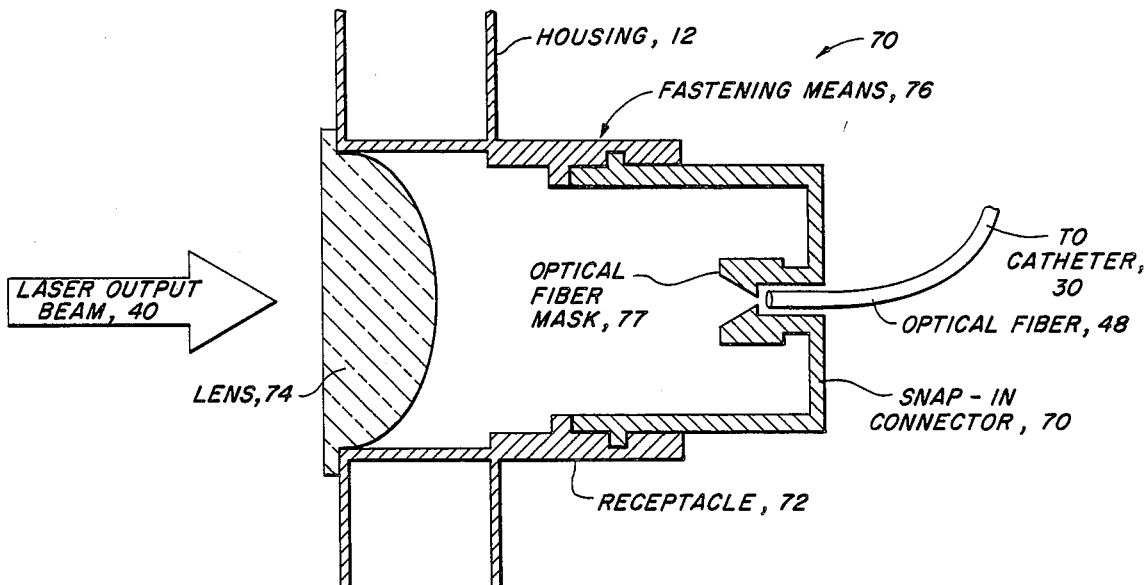
FIG. 4 is a detailed schematic diagram of the coupling assembly of the system shown in FIG. 1.

In FIG. 4, the output coupling port 70 is shown in more detail, consisting of a receptacle 72 sealed to the housing 12. Disposed within the receptacle is a lens 74, through which the laser output beam 40 is focused. The receptacle also has a hollow external opening which includes a fastening means 76 for releasably fastening a snap-in connector 78 carrying the optical fiber 48. In operation, the connector 78 is inserted into the fastening means 76 and the lens 74 focuses the laser output beam 40 into the optical fiber 48. Also shown in FIG. 4 is mask 77, which is disposed along the beam path to shield the peripheral region of the end face of fiber 48 from incident laser radiation in order to avoid chipping or otherwise damaging the fiber when the high energy pulsed radiation of beam 40 is focused into the fiber 48.

Figure 5:
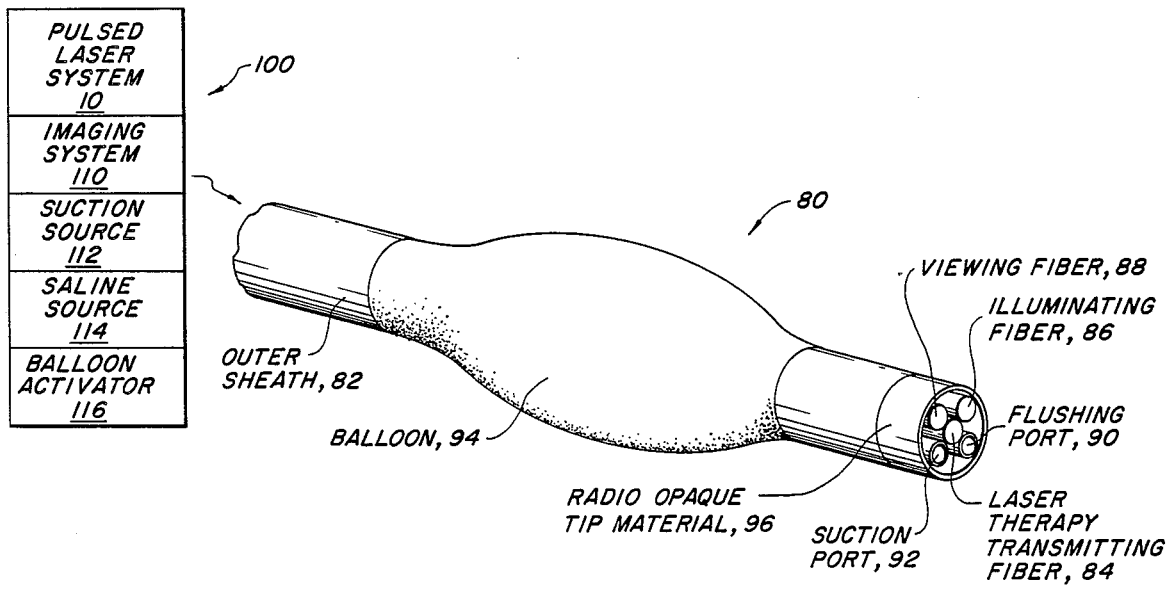
FIG. 5 is a detailed schematic diagram of a catheter instrument for use in the system of FIG. 1.

In FIG. 5, a schematic illustration of one embodiment of a laser catheter 80 for performing laser angioplasty is shown. FIG. 5 shows the details of the proximal end of the catheter 80 which is designed to be inserted into the patient and located proximal to the atherosclerotic plaque. Catheter 80 includes an outer sheath 82 and a plurality of internal lumens: a laser therapy transmitting fiber 84, an illuminating fiber 86, a viewing fiber 88, a flushing port 90 and a suction port 92. In the illustrated embodiment, the catheter also includes a balloon 94 to allow the practitioner to restrict blood flow in front of the catheter. Additionally, the illustrated embodiment includes a radio-opaque tip material 96 to aid the user in locating the catheter within the body by fluoroscopy.

In use, the invention can be practiced by connecting a sterilized disposable catheter, such as that illustrated in FIG. 5 or a similar device, to the laser therapy delivery system 10 of FIG. 1. The system 10 is then programmed via controls 46 for a particular set of operating conditions. For example, the output beam can have a peak energy density ranging from about 0.2 to about 20 Joules per square centimeter and a wavelength of about 308 nanometers. Similarly, the pulse duration of the output beam can range from about 5 nanoseconds to about 100 nanoseconds and the period between pulses ranges from about 1 millisecond to about 1 second. After programming the system, the catheter carrying the therapeutic fiber optics is inserted into the patient and passed through the artery to the lesion. The system is then activated by a foot petal control or the like to remove the lesion. In some instances, it may be preferred to employ balloon 94 to obstruct blood flow or to inject saline via port 90 or remove the blood and/debris via suction port 92.

A comprehensive support system 100 is also shown in FIG. 5 consisting of the laser delivery system 10, imaging system 110, suction source 112, saline 114, and balloon activator 116. After the initial lesion is removed, the catheter can be advanced to the next lesion for similar treatment.

What is claimed is:

1. A laser therapy system for delivering radiation through a fiber optic waveguide of a catheter, the system comprising:
   an energy source generating high energy pulsed radiation;
   a tunable laser optically coupled to the energy source to receive the pulsed radiation therefrom, the tunable laser having a resonant cavity defined by opposing reflectors, at least one of the reflectors being partially transmissive to yield an output beam capable of removing a target tissue by photodecomposition, and means for tuning said output beam over at least a portion of a spectrum ranging from about 300 to about 1000 nanometers;
   a housing enclosing the energy source and tunable laser and sealing them from the ambient environment;
   coupling means, secured to the housing and adapted to receive the fiber optic waveguide of the catheter and to focus the output beam into the waveguide; and
   control means electrically connected to the source and laser for varying the output of the laser within predefined ranges of energy, wavelength and pulse duration in response to conditions encountered during use of the system.

2. The system of claim 1 wherein the pulsed energy source is an excimer laser.

3. The system of claim 1 wherein the tunable laser further comprises a dye laser having a free-flowing liquid dye which is circulated through the resonant cavity of dye laser.

4. The system of claim 3 wherein the dye laser further includes means for changing the composition of the dye to effect tuning.

5. The system of claim 1 wherein the output beam has a peak energy density ranging from about 0.2 to about 20 Joules per square centimeter.

6. The system of claim 1 wherein the output beam has a peak energy density ranging from about 0.5 to about 10 Joules per square centimeter.

7. The system of claim 1 wherein the wavelength is greater than about 307 nanometers.

8. The system of claim 1 wherein the pulse duration of the output beam ranges from about 5 nanoseconds to about 100 nanoseconds.

9. The system of claim 8 wherein the period between pulses ranges from about 1 millisecond to about 1 second.

10. The system of claim 1 wherein the system further comprises an imaging system having an image detecting element also disposed with said catheter and an image processing means for processing an image from said image detecting element, whereby said image is available to an operator of said laser therapy system for guidance of said catheter and adjustment of said control means.

11. The system of claim 10 wherein the imaging system is an optical imaging system.

12. The system of claim 10 wherein the imaging system is an echographic imaging system.

13. The system of claim 10 wherein the imaging system is a photoacoustic imaging system.

14. A coupling device for use in a laser therapy system employing a fiber optic waveguide disposed within a catheter to transmit a beam of radiation from said laser therapy system to a patient, the coupling device comprising:
   a receptacle hermetically sealed to the laser system having an opening adapted to receive the waveguide;
   fastening means for releasably fastening the waveguide in a precise position in the receptacle during use and for releasing the waveguide once the phototherapy is completed;
   focusing means formed within the receptacle for receiving the beam of radiation and focusing the radiation on a path into an end surface of the waveguide; and
   shielding means disposed along said beam path for shielding a peripheral region of the end surface of the waveguide from damage due to the incidence of the focused radiation.

15. A method of performing angioplasty, the method comprising:
   coupling one end of a fiber optic waveguide carried within a catheter to a tunable source of radiation, said source producing a pulsed beam of radiation tunable over at least a portion of a spectrum ranging from about 300 to about 1000 nanometers and having a peak energy density ranging from about 0.2 Joules per square centimeter to about 20 Joules per square centimeter;
   disposing the catheter and waveguide within a blood vessel and locating the other end of the waveguide adjacent to an obstruction within the vessel;
   irradiating the obstruction to remove it by photodecomposition while varying the output of the radiation source within predefined ranges of energy and wavelength in response to conditions encountered during angioplasty.

16. The method of claim 15 wherein the step of irradiating the obstruction further includes irradiating with a radiation beam having a wavelength greater than about 307 nanometers.

17. The method of claim 15 wherein the step of disposing the catheter and waveguide within the blood vessel further includes positioning the waveguide by viewing the internal surface of the blood vessel through an optical system also disposed within the catheter.

18. The method of claim 15 wherein the step of disposing the catheter and waveguide within the blood vessel further includes positioning the waveguide by viewing the internal surface of the blood vessel through an imaging device also disposed within the catheter.

19. The method of claim 15 wherein the step of disposing the catheter within the blood vessel further comprises employing an inflation means to obstruct blood flow in front of said other end of the waveguide.

20. The method of claim 15 wherein the method further comprises removing any debris from the irradiated obstruction by evacuation through the catheter.

* * * * *